US010609960B2

(12) United States Patent
Deng et al.

(10) Patent No.: US 10,609,960 B2
(45) Date of Patent: Apr. 7, 2020

(54) ATOMIZING DEVICE FOR ELECTRONIC CIGARETTE

(71) Applicant: SHENZHEN FIRST UNION TECHNOLOGY CO., LTD., Shenzhen (CN)

(72) Inventors: Yindeng Deng, Shenzhen (CN); Yunping Zhong, Shenzhen (CN); Yonghai Li, Shenzhen (CN); Zhongli Xu, Shenzhen (CN)

(73) Assignee: SHENZHEN FIRST UNION TECHNOLOGY CO., LTD., Shenzhen (CN)

(*) Notice: Subject to any disclaimer, the term of this patent is extended or adjusted under 35 U.S.C. 154(b) by 108 days.

(21) Appl. No.: 15/695,031

(22) Filed: Sep. 5, 2017

(65) Prior Publication Data

US 2018/0070637 A1    Mar. 15, 2018

(30) Foreign Application Priority Data

Sep. 9, 2016    (CN) .................... 2016 2 1046106 U

(51) Int. Cl.
*A24F 13/00* (2006.01)
*A24F 17/00* (2006.01)
(Continued)

(52) U.S. Cl.
CPC ........... *A24F 47/008* (2013.01); *A61M 15/06* (2013.01); *A61M 2205/8206* (2013.01); *H05B 3/03* (2013.01)

(58) Field of Classification Search
CPC ....... A24F 47/008; A24F 47/002; A24F 47/00
(Continued)

(56) References Cited

U.S. PATENT DOCUMENTS

2014/0334803 A1* 11/2014 Li ........................... H05B 3/03
                                                             392/394
2016/0073692 A1*  3/2016 Alarcon ............... A24F 47/008
                                                             131/329
(Continued)

FOREIGN PATENT DOCUMENTS

CN         104605482 A      5/2015
CN         204317492 U      5/2015
(Continued)

OTHER PUBLICATIONS

European Search Report.

*Primary Examiner* — Abdullah A Riyami
*Assistant Examiner* — Thang H Nguyen
(74) *Attorney, Agent, or Firm* — IPro, PLLC

(57) ABSTRACT

An atomizing device for an electronic cigarette includes: an atomizing sleeve defining a liquid storage chamber for containing e-liquid; a heating element positioned in the atomizing sleeve and configured to heat the e-liquid to generate vapor; a liquid absorbing unit configured to absorb the e-liquid in the liquid storage chamber and transfer the e-liquid to the heating element; and a holder defining a hollow cavity. The holder fixes the liquid absorbing unit and the heating element, and the heating element is positioned in the hollow cavity. A temporary storage cavity is positioned under the holder. The holder defines at least one airflow through hole which is configured to communicate with the temporary storage cavity with the hollow cavity, the temporary storage cavity is configured to communicate with an air inlet, and the air inlet is in a higher position than a bottom of the temporary storage cavity.

6 Claims, 5 Drawing Sheets

(51) Int. Cl.
*A24F 25/00* (2006.01)
*A24F 47/00* (2020.01)
*A61M 15/06* (2006.01)
*H05B 3/03* (2006.01)

(58) Field of Classification Search
USPC .................................................. 131/329, 328
See application file for complete search history.

(56) References Cited

U.S. PATENT DOCUMENTS

| | | | | |
|---|---|---|---|---|
| 2016/0081394 | A1* | 3/2016 | Alarcon | A24D 3/04 |
| | | | | 131/328 |
| 2017/0303596 | A1* | 10/2017 | Chen | A61M 11/04 |
| 2018/0352865 | A1* | 12/2018 | Qiu | A24F 47/008 |
| 2019/0124997 | A1* | 5/2019 | Qiu | A24F 47/00 |

FOREIGN PATENT DOCUMENTS

| | | | |
|---|---|---|---|
| CN | 105795527 | A | 7/2016 |
| CN | 205456063 | U | 8/2016 |
| CN | 206043435 | U | 3/2017 |
| EP | 2801270 | A2 | 11/2014 |
| KR | 200477818 | Y1 | 7/2015 |

* cited by examiner

ATOMIZING DEVICE FOR ELECTRONIC CIGARETTE

CROSS-REFERENCE TO RELATED APPLICATIONS

The present disclosure claims priority to Chinese Patent Application No. 201621046106.6, filed with the Chinese Patent Office on Sep. 9, 2016, titled "ATOMIZING DEVICE FOR ELECTRONIC CIGARETTE", the entire contents of which are incorporated herein by reference.

TECHNICAL FIELD

The present disclosure relates to the field of electronic cigarettes, and particularly, to an atomizing device for an electronic cigarette.

BACKGROUND

As substitute goods for cigarettes, electronic cigarettes have aroused more and more attention because of its advantages of safety, convenience, health and environmental friendliness in use. Typically, the electronic cigarettes on the market include an atomizing device and a battery module, and the atomizing device includes an atomizing core and a liquid storage chamber for storing e-liquid. In widely-used schemes, the atomizing core heats and atomizes the e-liquid to generate vapor, thus achieving the feeling of tobacco smoking.

For example, the atomizing core of the atomizing device of a typical electronic cigarette includes a liquid absorbing unit, a heating element and a holder. The liquid absorbing unit extends out of the holder and absorbs the e-liquid from the liquid storage chamber.

SUMMARY

An embodiment of the present disclosure provides an atomizing device for electronic cigarette, including:

an atomizing sleeve defining a liquid storage chamber for containing e-liquid;

a heating element, which is positioned in the atomizing sleeve, configured to heat and evaporate the e-liquid to generate vapor;

a liquid absorbing unit, which contacts with the heating element, configured to absorb the e-liquid in the liquid storage chamber and transfer the e-liquid to the heating element; and a holder defining a hollow cavity, the holder configured to fix the liquid absorbing unit and the heating element, wherein the heating element is positioned in the hollow cavity;

wherein, a temporary storage cavity is positioned under the holder, the holder defines at least one airflow through hole which is configured to communicate with the temporary storage cavity with the hollow cavity, wherein the temporary storage cavity is configured to communicate with an air inlet, and the air inlet is positioned in a higher position than a bottom of the temporary storage cavity.

BRIEF DESCRIPTION OF THE DRAWINGS

One or more embodiments are illustrated by way of example, and not by limitation, in the figures of the accompanying drawings, wherein elements having the same reference numeral designations represent like elements throughout. The drawings are not to scale, unless otherwise disclosed.

DETAILED DESCRIPTION

The structure and use principle of an atomizing device for an electronic cigarette of the present disclosure are further illustrated by embodiments as follows.

Figure 1:
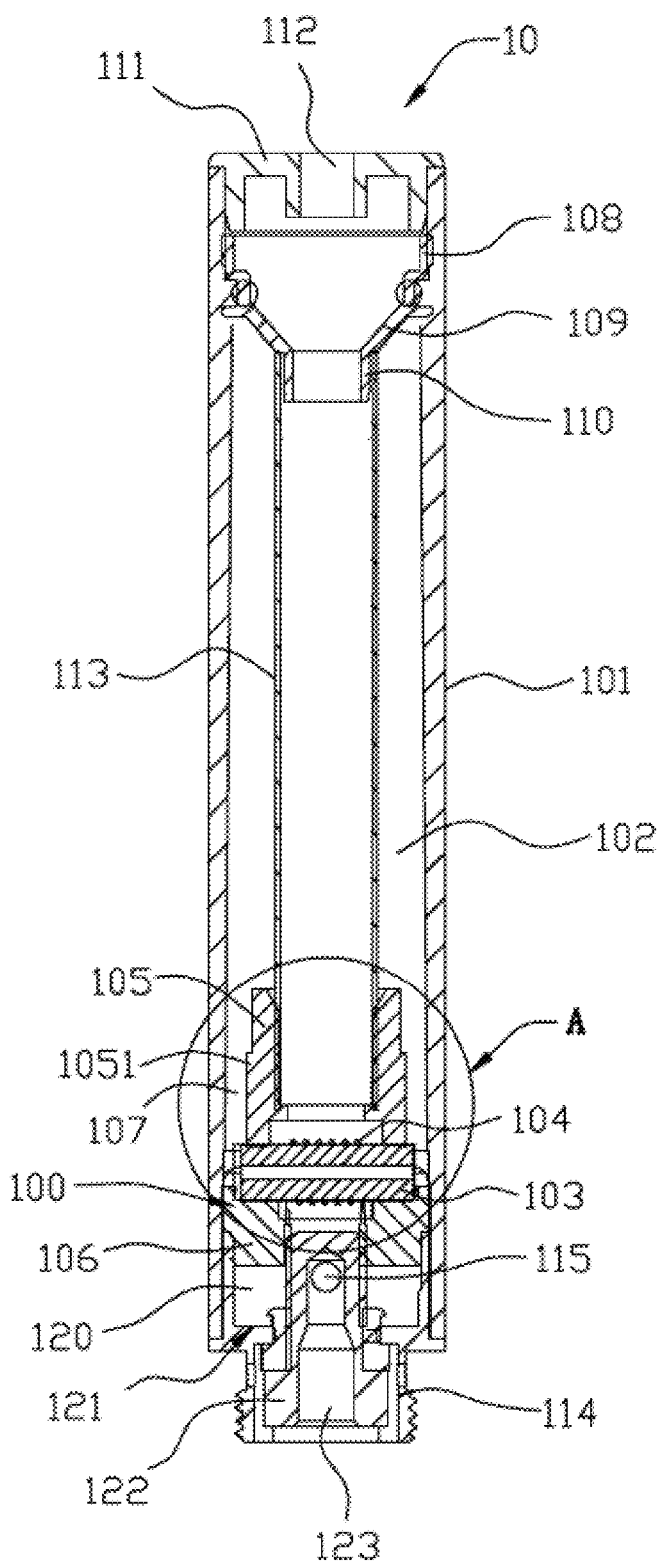
FIG. 1 is an axial cutaway view of an atomizing device for an electronic cigarette in accordance with an embodiment of the present disclosure.
Figure 2:
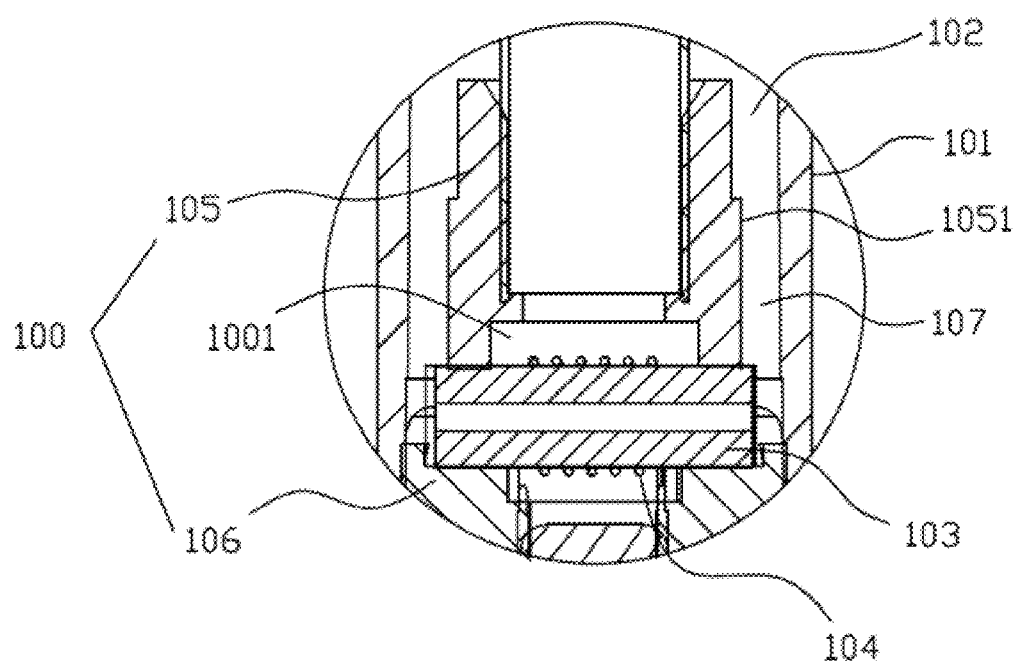
FIG. 2 is a partial enlarged view of part A shown in FIG. 1.

As shown in FIGS. 1 and 2, an embodiment of the present disclosure provides an atomizing device 10 configured to be assembled with a battery assembly to constitute an electronic cigarette. The atomizing device 10 includes an atomizing sleeve 101, a heating element 104 and a liquid absorbing unit 103 which are both positioned in the atomizing sleeve 101, and a holder 100 configured to fix the heating element 104 and the liquid absorbing unit 103. The atomizing sleeve 101 defines a liquid storage chamber 102 for containing e-liquid, a vapor transportation pipe 113 is positioned in the center of the liquid storage chamber 102, wherein the atomizing sleeve 101, the vapor transportation pipe 113, and the holder 100 cooperatively define the liquid storage chamber 102 therebetween.

The heating element 104 is positioned in the atomizing sleeve 101 and configured to heat and evaporate the e-liquid to generate vapor. The liquid absorbing unit 103 contacts with the heating element 104. The liquid absorbing unit 103 is configured to absorb the e-liquid from the liquid storage chamber 102 and transfer the e-liquid to the heating element 104. The holder 100 defines a hollow cavity 1001, and the heating element 104 is positioned in the hollow cavity 1001. The hollow cavity 1001 is configured to communicate with the vapor transportation pipe 113 positioned thereon, and the heating element 104 heats the e-liquid to generate vapor which enters the vapor transportation pipe 113 along with the airflow. An electrical connection component 114 is positioned on a lower end of the atomizing sleeve 101 to connect to a battery assembly; the electrical connection component 114 includes an electrode 122 defining an air inlet 115, and upon inhaling, external air enters the hollow cavity 1001 of the holder 100 via the air inlet 115.

In an exemplary embodiment, the liquid absorbing unit 103 is a microporous ceramic rod with a center hole 1031 defined therein, or the liquid absorbing unit 103 is made of microcellular foaming material such as glass fiber material, which can absorb e-liquid from the liquid storage chamber 102 in virtue of capillary action. The center hole 1031 enables the e-liquid to enter the interior of the microporous ceramic rod smoothly, so that the microporous ceramic rod can absorb the e-liquid adequately; the heating element 104 is a heating coil wound on the microporous ceramic rod, and the heating coil heats and evaporates the e-liquid exuding from the surface of the microporous ceramic rod to generate vapor.

The holder 100 includes at least one step 1051 protruding towards the liquid storage chamber 102, whereby a ladderlike liquid flow channel 107 is defined between an outer wall of the step 1051 and an inner wall of the atomizing sleeve 101. At least a part of the liquid absorbing unit 103 extends out of the outer wall of the step 1051 to absorb the e-liquid from the liquid flow channel 107. Because the step 1051 protrudes towards the liquid storage chamber 102, the width between the outer wall of the step 1051 and the inner wall of the atomizing sleeve 101 is smaller than the width of the liquid storage chamber 102. If the width of the liquid flow channel 107 is appropriately set, the tension action of the outer wall of the step 1051 and the inner wall of the atomizing sleeve 101 on the e-liquid molecules can slow down the flow velocity of the e-liquid and control the outflow volume of the e-liquid, thus preventing the leakage of the e-liquid from the gap between the liquid absorbing unit 103 and the holder 100 in nonuse of the atomizing device 10. In an exemplary embodiment, to better control the release rate of the e-liquid, the distance between the outer wall of the step 1051 and the inner wall of the atomizing sleeve 101 is set to be between 0.6 and 1.1 mm, the liquid absorbing unit 103 is positioned at the bottom of the liquid storage chamber 102, so that the e-liquid in the liquid storage chamber 102 slowly permeates into the liquid absorbing unit 103 via the liquid flow channel 107.

In an exemplary embodiment, a suction nozzle 108 is positioned in an upper end of the atomizing sleeve 101. The suction nozzle 108 extends inwards to form a vapor pipe mounting part 110, an inner diameter of the vapor pipe mounting part 110 is smaller than an inner diameter of the suction nozzle 108, the vapor pipe mounting part 110 and the suction nozzle 108 are connected via a funnel part 109, and an upper end of the vapor transportation pipe 113 is sleeved on the vapor pipe mounting part 110. Upon inhaling, the vapor flowing upward in the vapor transportation pipe 113 may contain small drops which are condensation products or not completely atomized, when the vapor enters the funnel part 109 via the vapor pipe mounting part 110, because the inner diameter of the funnel part 109 gradually increases, the airflow velocity decreases, the small drops tend to attach to the inner wall of the funnel part 109 or the suction nozzle 108, then flow back along the inclined plane of the funnel part 109 and are heated and atomized again. Moreover, the vapor transportation pipe 113 in this illustrated embodiment is not integratedly formed with the atomizing sleeve 101. The vapor transportation pipe 113 is a thin-walled metal tube or a thin-walled plastic pipe, which, compared with prior arts, greatly increases the inner diameter for airflow passing through, reduces the flow velocity of the vapor, accelerates the condensation of the drops on the pipe wall, and decreases the amount of the drops in the vapor reaching the suction nozzle 108.

Further, the suction nozzle 108 includes a nozzle cap 111 with a suction hole 112 defined therein, and a diameter of the suction hole 112 is smaller than the inner diameter of the suction nozzle 108. In this illustrated embodiment, the diameter of the suction hole 112 is basically equal to the inner diameter of the vapor pipe mounting part 110. The vapor flow in the vapor transportation pipe 113 is buffered in the relatively large space of the funnel part 109 and the suction nozzle 108, then inhaled from the suction hole 112, and the condensed e-liquid flows back along an inclined plane of the funnel part 109, thus effectively reducing the probability of inhaling the condensed e-liquid by users.

Figure 3:
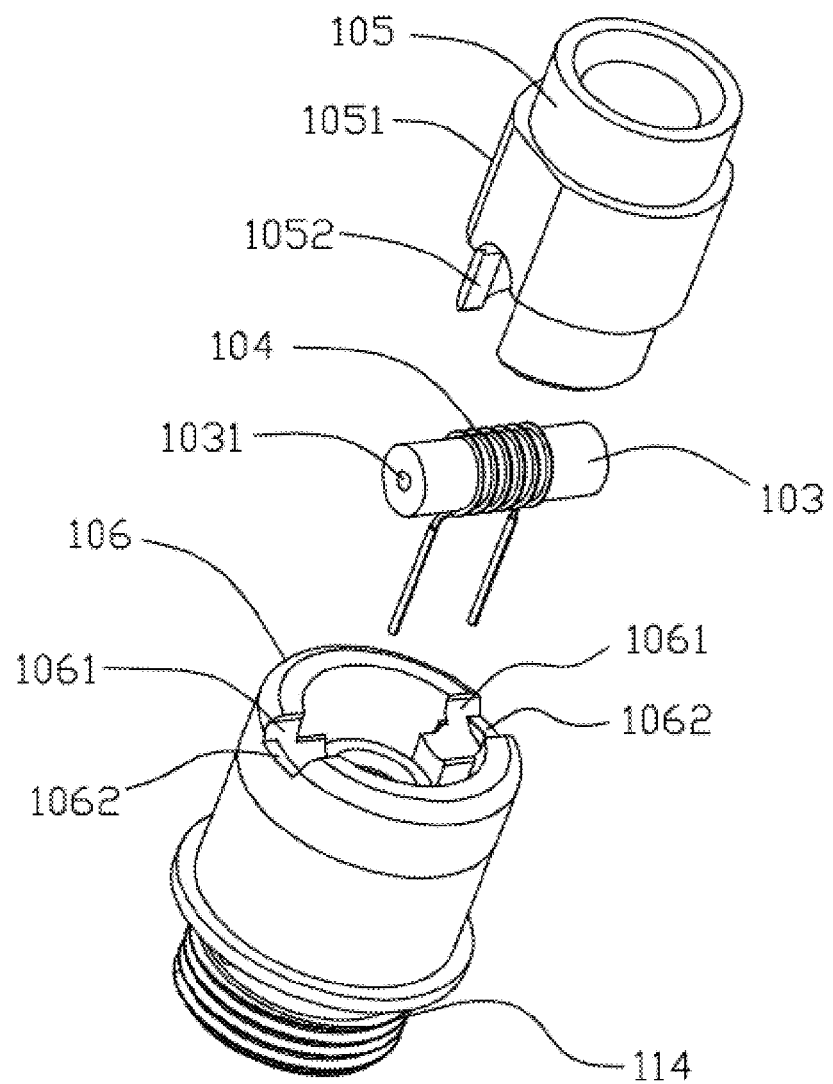
FIG. 3 a schematic view illustrating a cooperation of an upper holding unit and a lower holding unit to clamp a liquid absorbing unit of the atomizing device.

As shown in FIG. 3, the holder 100 includes an upper holding unit 105 and a lower holding unit 106 which are engaged with each other. The upper holding unit 105 defines a first notch 1052, the lower holding unit 106 defines a second notch 1061, and each first gap 1052 is opposite to a corresponding one of the second notch 1061. The liquid absorbing unit 103 is clamped in the first notch 1052 and the second notch 1061 by the upper holding unit 105 and the lower holding unit 106. Specifically, the upper holding unit 105 defines two of the first notch 1052 that are symmetrical to each other, and the lower holding unit 106 defines two of the second notch 1061 that are symmetrical to each other. The lower part of the upper holding unit 105 can insert into the interior of the lower holding unit 106, and the first notch 1052 and the second notch 1061 are oppositely positioned to form two openings, two ends of the liquid absorbing unit 103 extend out of the openings and are exposed in the liquid storage chamber 102. Both the upper holding unit 105 and the lower holding unit 106 are made of silica gel material, so the liquid absorbing unit 103 is tightly attached to the upper holding unit 105 and the lower holding unit 106, thereby reducing the probability of the leakage of the e-liquid.

The outer wall of the lower holding unit 106 is tightly attached to the inner wall of the atomizing sleeve 101, the step 1051 is located on the peripheral wall of the upper holding unit 105, the upper end surface of the lower holding unit 106 is also the bottom of the liquid storage chamber 102, the step 1051 is in a shape of annular, and the narrow annular space between the step 1051 and the inner wall of the atomizing sleeve 101 constitutes the liquid flow channel 107.

In an exemplary embodiment, an upward lug 1062 is positioned on the outer side of each second notch 1061 of the lower holding unit 106, the lug 1062 butts against the end face of the liquid absorbing unit 103, the liquid absorbing unit 103 does not completely pass through the second notch 1061, so that only part of the end face of the liquid absorbing unit 103 can touch the e-liquid, thus reducing the suction rate of the e-liquid, and further reducing the probability of leakage of the e-liquid via the second notch 1061.

Figure 4:
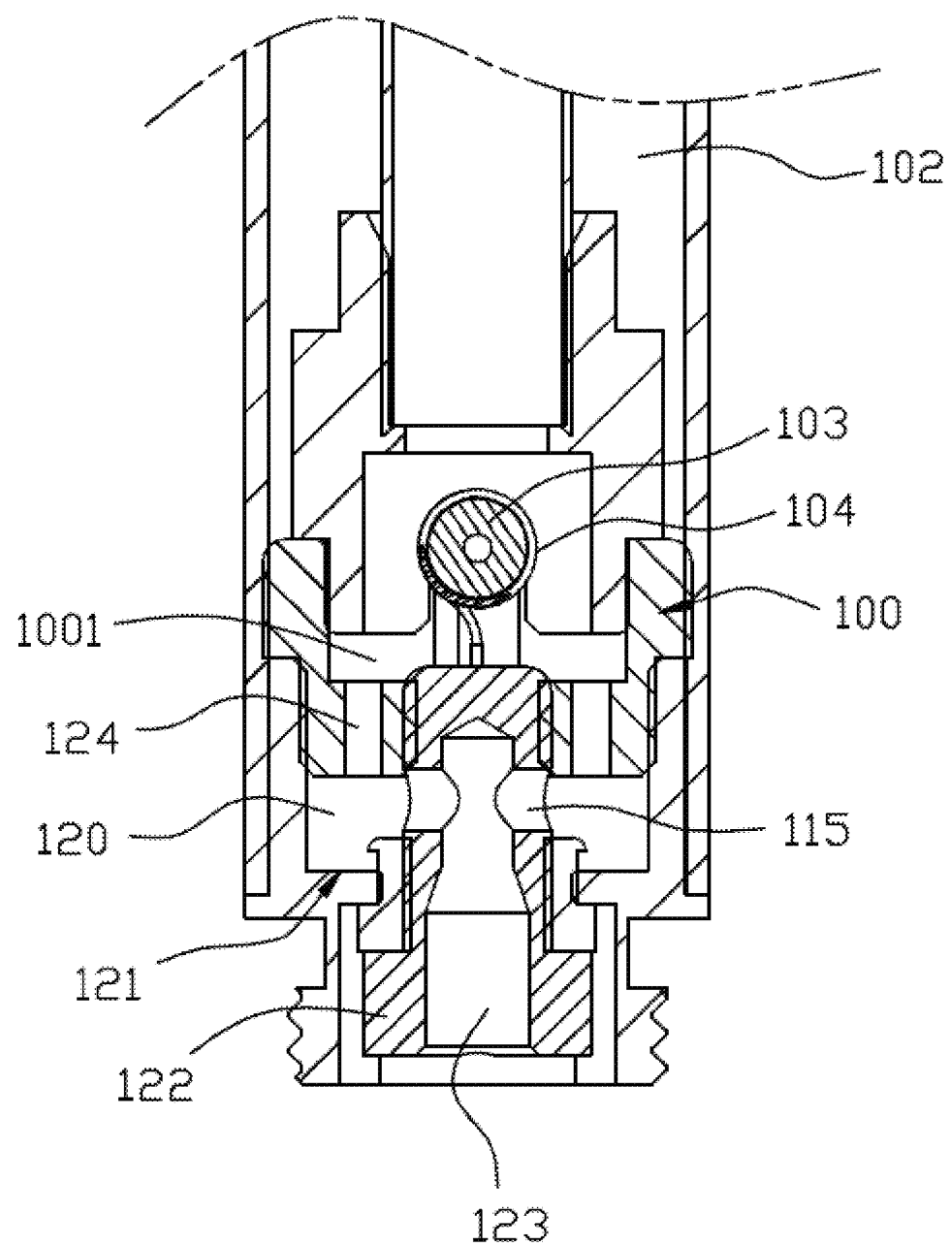
FIG. 4 is an axial cutaway view of the atomizing device, viewed from another angle.

As shown in FIG. 4, a temporary storage cavity 120 is positioned under the holder 100, the holder 100 defines at least one airflow through hole 124 which enables the temporary storage cavity 120 to be configured to communicate with the hollow cavity 1001 of the holder 100, the temporary storage cavity 120 is configured to communicate with the air inlet 115, and the air inlet 115 is positioned in a higher position than the bottom 121 of the temporary storage cavity 120. The e-liquid accumulated in the hollow cavity 1001 or flowing back from the vapor transportation pipe 113 can flow through the airflow through hole 124 and is stored in the bottom 121 of the temporary storage cavity 120, and will not flow out of the atomizing device 10 via the air inlet 115, thereby avoiding the contamination of the battery module. Upon inhaling, the external air can flow through the air inlet 115, the temporary storage cavity 120, and the airflow through hole 124 successively, and then enters the hollow cavity 1001.

Specifically, the electrode 122 is positioned in the center of the temporary storage cavity 120, a blind hole 123 is positioned in the lower end of the electrode 122, the air inlet 115 is defined in the sidewall of the electrode 122 and is configured to communicate with the blind hole 123, the airflow through hole 124 is disaligned with respect to the underneath of the heating element 104, wherein the blind hole 123, the air inlet 115, and the airflow through hole 124 cooperatively form a non-linear airflow channel, which further increases the difficulty of the leakage of the e-liquid out of the atomizing device 10. The electrode 122 is located in the center of the holder 100 and disaligned with respect to the underneath of the heating element 104, the top thereof is an enclosed structure, so the e-liquid dripping from the heating element 104 and the liquid absorbing unit 103 cannot directly flow out of the blind hole 123, and must flow through the non-linear liquid passage, and thus is stored in the temporary storage cavity 120.

Figure 5:
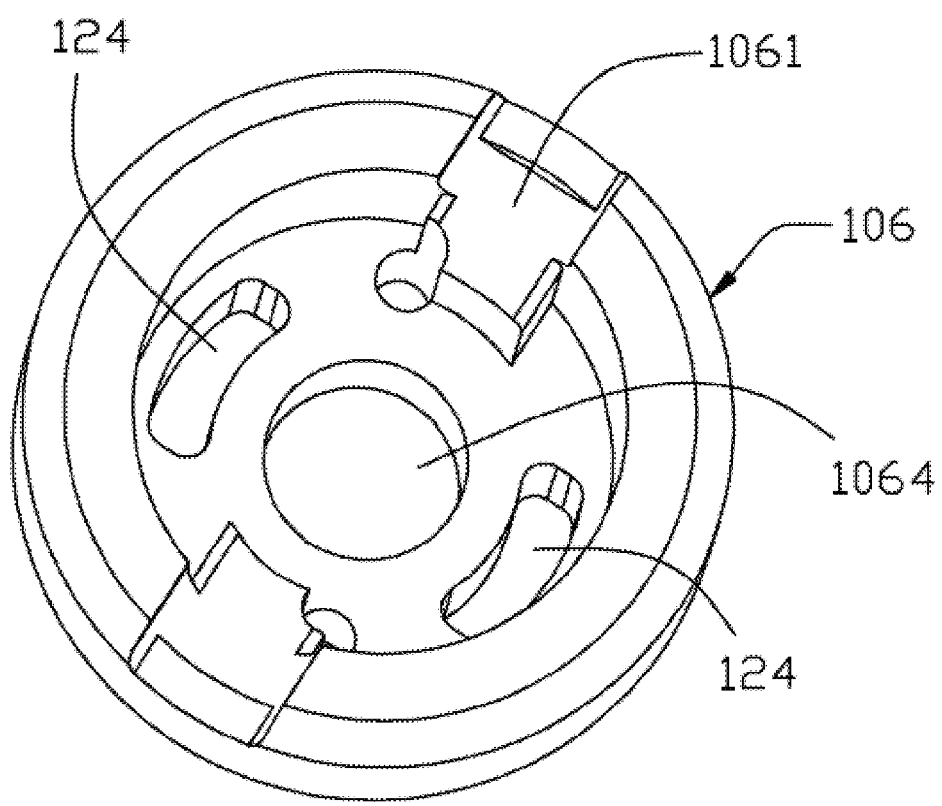
FIG. 5 is a schematic diagram of the lower holding unit.

FIG. 5 illustrates a schematic diagram of the lower holding unit 106. The lower holding unit 106 defines a center bore 1064, and the top of the electrode 122 is hermetically assembled in the center bore 1064. In this illustrated embodiment, two symmetrically-distributed airflow through holes 124 are positioned in the lower holding unit 106. Preferably, the airflow through hole 124 is a long strip opening with the section shape of rectangle, oval, or oval-like, the width thereof is between 0.4 and 1.0 mm, and the length thereof is random. In the width range of the airflow through hole 124, due to capillary effect, the surface tension formed on the sidewall of the airflow through hole 124 can basically offset the gravity of the e-liquid, the condensed e-liquid in the hollow cavity 1001 of the holder 100 cannot easily flow into the temporary storage cavity 120 under the airflow through hole 124, and can be evaporated again to generate vapor in the next inhaling.

The above embodiments are merely illustrative some exemplary embodiments of the disclosure, but are not intended to limit the scope of the present disclosure. Any equivalent structure or equivalent process variation made based on the specification and drawings of the present disclosure, falls within the scope of the present disclosure.

What is claimed is:

1. An atomizing device for an electronic cigarette, comprising:
    an atomizing sleeve defining a liquid storage chamber for containing e-liquid;
    a heating element, which is positioned in the atomizing sleeve, configured to heat and evaporate the e-liquid to generate vapor;
    a liquid absorbing unit, contacting with the heating element, configured to absorb the e-liquid in the liquid storage chamber and transfer the e-liquid to the heating element; and
    a holder defining a hollow cavity, the holder configured to fix the liquid absorbing unit and the heating element, wherein the heating element is positioned in the hollow cavity;
    wherein,
    a temporary storage cavity is positioned under the holder, the holder defines at least one airflow through hole which is configured to communicate the temporary storage cavity with the hollow cavity, wherein the temporary storage cavity is configured to communicate with an air inlet, and the air inlet is in a higher position than a bottom of the temporary storage cavity;
    the holder comprises an upper holding unit and a lower holding unit which are engaged with each other, the upper holding unit and the lower holding unit each defines a notch which are opposite to each other, and the liquid absorbing unit is clamped in the notch by the upper holding unit and the lower holding unit;
    an upward lug is positioned on an outer side of each notch of the lower holding unit, the lug butts against an end face of the liquid absorbing unit.

2. The atomizing device according to claim 1, wherein the atomizing device comprises a suction nozzle positioned in an upper end of the atomizing sleeve, the suction nozzle extends inwards to form a vapor pipe mounting part, an inner diameter of the vapor pipe mounting part is smaller than an inner diameter of the suction nozzle, the vapor pipe mounting part and the suction nozzle are connected via a funnel part, and a vapor transportation pipe is positioned between the vapor pipe mounting part and the holder.

3. The atomizing device according to claim 2, wherein the suction nozzle comprises a nozzle cap, the nozzle cap defines a suction hole, and a diameter of the suction hole is smaller than the inner diameter of the suction nozzle.

4. An atomizing device for an electronic cigarette, comprising:
    an atomizing sleeve defining a liquid storage chamber for containing e-liquid;
    a heating element, which is positioned in the atomizing sleeve, configured to heat and evaporate the e-liquid to generate vapor;
    a liquid absorbing unit, contacting with the heating element, configured to absorb the e-liquid in the liquid storage chamber and transfer the e-liquid to the heating element; and
    a holder defining a hollow cavity, the holder configured to fix the liquid absorbing unit and the heating element, wherein the heating element is positioned in the hollow cavity;
    wherein,
    a temporary storage cavity is positioned under the holder, the holder defines at least one airflow through hole which is configured to communicate the temporary storage cavity with the hollow cavity, wherein the temporary storage cavity is configured to communicate with an air inlet, and the air inlet is in a higher position than a bottom of the temporary storage cavity;
    the holder comprises an upper holding unit and a lower holding unit which are engaged with each other, the upper holding unit and the lower holding unit each defines a notch which are opposite to each other, and the liquid absorbing unit is clamped in the notch by the upper holding unit and the lower holding unit;
    an outer wall of the lower holding unit is tightly attached to an inner wall of the atomizing sleeve, an upper end surface of the lower holding unit is a bottom of the liquid storage chamber; a step is located on a peripheral wall of the upper holding unit, and a liquid flow channel is defined between the step and the inner wall of the atomizing sleeve.

5. The atomizing device according to claim 4, wherein the atomizing device comprises a suction nozzle positioned in an upper end of the atomizing sleeve, the suction nozzle extends inwards to form a vapor pipe mounting part, an inner diameter of the vapor pipe mounting part is smaller than an inner diameter of the suction nozzle, the vapor pipe mounting part and the suction nozzle are connected via a funnel part, and a vapor transportation pipe is positioned between the vapor pipe mounting part and the holder.

6. The atomizing device according to claim 5, wherein the suction nozzle comprises a nozzle cap, the nozzle cap defines a suction hole, and a diameter of the suction hole is smaller than the inner diameter of the suction nozzle.

* * * * *